United States Patent [19]

Graiver et al.

[11] Patent Number: 5,739,246
[45] Date of Patent: Apr. 14, 1998

[54] PREPARATION OF CARBONYL FUNCTIONAL POLYSILOXANES

[75] Inventors: Daniel Graiver, Midland, Mich.; Aaron Quoc Khieu, Coon Rapids, Minn.; Binh Thanh Nguyen, Midland, Mich.

[73] Assignee: Dow Corning Corporation, Midland, Mich.

[21] Appl. No.: 812,808

[22] Filed: Mar. 6, 1997

[51] Int. Cl.$^6$ .................................................. C08G 77/20
[52] U.S. Cl. ........................... 528/32; 528/14; 528/15; 528/18; 528/19; 528/21; 528/23; 528/25; 556/436; 556/450
[58] Field of Search .......................... 528/32, 25, 14, 528/15, 18, 19, 21, 23; 556/436, 450

[56] References Cited

U.S. PATENT DOCUMENTS

| | | | |
|---|---|---|---|
| 2,588,083 | 3/1952 | Burkhard | 260/448 |
| 2,591,736 | 4/1952 | Sommer | 260/448 |
| 3,145,232 | 8/1964 | Thompson | 260/586 |
| 3,202,704 | 8/1965 | Perry | 260/533 |
| 3,344,104 | 9/1967 | Hyde | 260/32.8 |
| 4,609,574 | 9/1986 | Keryk | 427/407 |
| 5,021,601 | 6/1991 | Frances et al. | 556/436 |
| 5,215,554 | 6/1993 | Kramer et al. | 55/16 |

FOREIGN PATENT DOCUMENTS

| | | |
|---|---|---|
| 1132114 | 6/1962 | Germany. |
| 757355 | 9/1956 | United Kingdom. |

OTHER PUBLICATIONS

Russian Chemical Reviews, vol. 36, No. 4, pp. 284–294, Apr. 1967.
Journal Americal Chemical Society, vol. 72, pp. 1935–1939, May 1950.
Z. Chem., 5, Jg, Heft 3, pp. 97–103, 1965.
Organic Chemistry, Prentice Hall, pp. 315–316, 1987.
Journal American Chemical Society, vol. 113, pp. 8168–8169, 1991.
Journal American Chemical Society, vol. 79, pp. 3073–3077, Jun. 1957.
Journal Organic Chemistry, vol. 35, No. 12, pp. 4180–4183, 1970.
Journal Organic Chemistry, vol. 23, pp. 627–628, Apr. 1958.
Journal Organic Chemistry, vol. 24, pp. 427–428, Mar. 1959.
F. Asinger, Ber., Jahrg. 75, 656–660, 1942.
Chemical Reviews, vol. 27, No. 3, pp. 437–493, Dec. 1940.
Chemical Reviews, vol. 58, No. 5, pp. 925–1010, Oct. 1958.
Journal Organic Chemistry, vol. 35, No. 11, pp. 3879+, 1970.
Bulletin of the Academy of Sciences, USSR, Division of Chemical Science, No. 8, pp. 1405–1407, Aug. 1966.
Journal of General Chemistry of the USSR, vol. 38, No. 10, pp. 2234–2236, Oct. 1968.
Journal of General Chemistry of the USSR, vol. 38, No. 2, pp. 380–385, Feb. 1968.

*Primary Examiner*—Melvyn I. Marquis
*Attorney, Agent, or Firm*—James L. Decesare

[57] ABSTRACT

Polysiloxanes having pendant and/or telechelic carbonyl functionality, i.e., aldehyde functionality $\equiv$Si—R—CH=O or ketone functionality $\equiv$Si—R—CR=O, are manufactured in high yield by ozonolysis of polydiorganosiloxanes containing alkenyl groups, followed by treatment with a reducing agent such as zinc and acetic acid. The process is relatively fast and economical using readily available starting materials such as hexenyl-functional polymers. In particular, aldehyde functionality on the polymer can be used as a polymeric crosslinking agent.

7 Claims, No Drawings

PREPARATION OF CARBONYL FUNCTIONAL POLYSILOXANES

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention is directed to organosiloxanes containing organocarbonyls, methods for preparing organosiloxane organocarbonyls, and more particularly is directed to aldehyde or ketone functional polydiorganosiloxane polymers and copolymers.

The reaction of ozone ($O_3$) with a carbon-carbon double bond is known. Historically, however, the reaction has primarily been used as an analytical method to determine the position of a double bond along a hydrocarbon chain. Based on early studies and published reports, it is generally agreed among artisans that an ozonide intermediate is formed upon exposure of a double bond to ozone. This reaction in which ozone attaches itself at a double bond to form an ozonide is shown generally as follows:

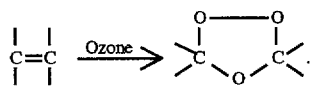

Based on prior studies and reports, the ozonide intermediate is believed to be a five-member peroxy-ether ring shown below:

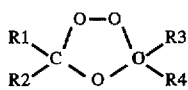

in which R1, R2, R3, and R4, are hydrogen, an alkyl group such as methyl, or an aryl group such as phenyl. When R1, R2, R3, and R4, are each hydrogen, for example, the ozonide is 1,2,4-trioxolane. When R1 and R3 are hydrogen, and R2 and R4 are methyl, for example, the ozonide is 3,5-dimethyl-1,2,4-trioxolane.

These ozonide intermediates are not stable, however, and they are known to readily rearrange to various hydroperoxides, dimeric and polymeric peroxides, and other oxygen containing compounds. According to the literature, it is generally agreed among artisans that in most cases, these ozonides break down rapidly, and initially form more stable zwitterion intermediates.

It is also known that ozonide intermediates can be reduced to carbonyl compounds as generally depicted below. Therefore, following conversion of an Alkene to an Ozonide, the Ozonide can be reduced to an Aldehyde. In the reaction scheme, the reducing agent is zinc and acetic acid.

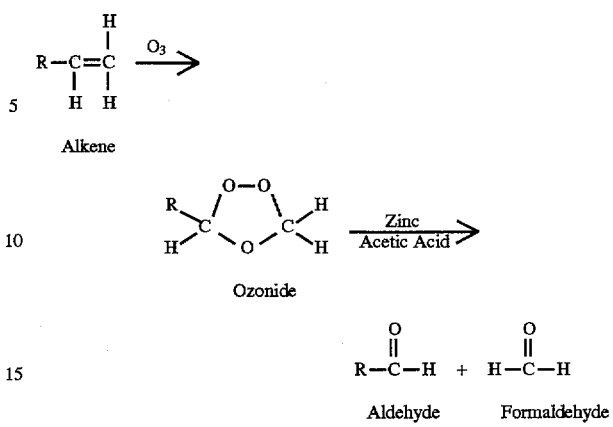

Ketones are similarly obtained as follows:

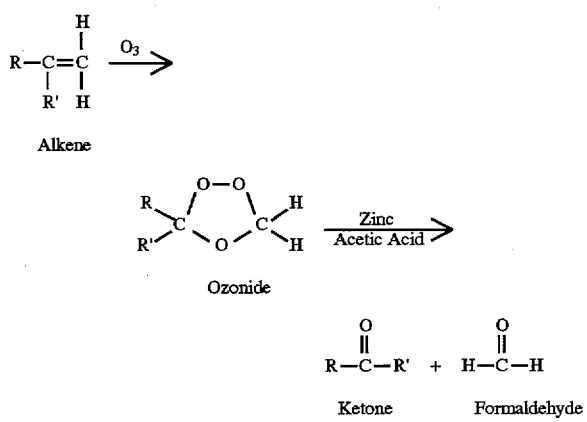

Under suitable conditions, a clean and efficient reaction can be attained, and the Ozonide can be converted to a corresponding carbonyl compound (Aldehyde/Ketone) using an appropriate solvent, reducing agent, and reaction temperature.

The solvent plays an important role in stabilization of the ozonide intermediate and its reduction to a carbonyl. The choice of solvent depends upon the particular alkene being used, and some solvents have been found to be more efficient than others. Thus, some of the more preferred solvents are aprotic solvents such as carbon tetrachloride $CCl_4$, methylene chloride $CH_2Cl_2$, and chloroform $CHCl_3$, which lead to high yields of the ozonide and its subsequent reduction to the corresponding aldehyde or ketone, Reducing agents that have been employed include sodium iodide and water, potassium iodide and water, sodium iodide and acetic acid, potassium iodide and acetic acid, zinc and water, magnesium and water, zinc and acetic acid, and magnesium and acetic acid. Other reducing agents that can be used in preparing aldehydes or ketones from ozonide intermediates are sodium bisulfite $NaHSO_3$, ferrous sulfate $FeSO_4$, potassium ferrocyanide $K_4[Fe(CN)_6]$, stannous chloride $SnCl_2$ and hydrochloric acid, tin and hydrochloric acid, ferrous ammonium sulfate $(NE_4)_2Fe(SO_4)_2$, silver nitrate $AgNO_3$, trimethyl phosphite $(CH_3O)_3P$, quinol (hydroquinone) $C_6H_4(OH)_2$, pyridine $N(CH)_4CH$, piperidine $C_5H_{11}N$, sulfur dioxide, and dimethyl sulfide $(CH_3)_2S$ Yet in spite of the fact that information is available to artisans on converting an unsaturated carbon-carbon double bond to an aldehyde or ketone by ozonolysis and reduction, it has not been applied to polysiloxanes having carbon-carbon double bonds. This is because ozonolysis and subsequent reduction are conducted at low temperature to stabilize the ozonide intermediate and prevent its uncontrolled decomposition. Under such low temperature conditions in aprotic chlorinated solvents for example, polysiloxanes precipitate and crystallize out of solution.

Therefore, for making organosiloxanes containing carbonyl functionality, methods other than ozonolysis have been attempted, but have not been useful, either because of poor yield, the occurrence of extensive side reactions, or significant costs associated with starting materials or the process itself. Even when disiloxanes having non-labile substituents, i.e., RMe$_2$SiOSiMe$_2$H where R is —CH$_3$ or H, have been reacted with unsaturated acetals R—CH(OR)$_2$ rather than an unsaturated carbonyl such as an aldehyde, a mixture of silyl compounds has been obtained. However, upon hydrolysis of the silyl acetal to obtain the silyl aldehyde, significant redistribution reactions occurred.

Our invention resolves these problems, and provides an efficient method of obtaining carbonyl functional polysiloxanes having pendant groups from the main siloxane chain, or terminal telechelic functional groups, or both.

BRIEF SUMMARY OF THE INVENTION

Our invention relates to a method of making organosiloxane carbonyl compounds by first forming an organosiloxane containing ozonide functionality. This is accomplished by exposing a polydiorganosiloxane polymer or copolymer containing alkenyl groups to ozone. After forming the organosiloxane containing ozonide functionality, it is then reduced to the corresponding organosiloxane containing carbonyl functionality.

Our invention also relates to the organosiloxane carbonyl compounds prepared by this method.

These and other features and objects of our invention will become apparent from a consideration of the detailed description.

BRIEF DESCRIPTION OF THE SEVERAL VIEWS OF THE DRAWING

Not applicable.

DETAILED DESCRIPTION OF THE INVENTION

Polydiorganosiloxanes containing alkenyl groups suitable for use according to our invention are represented by the following formulas:

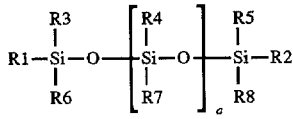

and

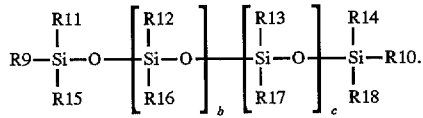

In these formulas, R1–R18 represent an alkyl group containing 1–6 carbon atoms such as methyl, ethyl, propyl, butyl, pentyl, and hexyl, for example; an aryl group such as phenyl; or an alkenyl group with the unsaturated carbon atoms separated from the silicon atom by at least two saturated carbon atoms. Generally, a has a value of 4–200; b has a value of 1–200, and c has a value of about 1–10. Preferably, a and b have values of 30–150, most preferably 70–100.

Preferably, R1 and R2 should both be alkenyl groups. In addition, R1, R2, and either R4 or R7 should be alkenyl groups simultaneously. Similarly, R9 and R10 should both be alkenyl groups; and R9, R10, and either R13 or R17 should be alkenyl groups simultaneously. R12 and R16 should be the same, preferably alkyl groups.

Especially preferred polymers and copolymers for use herein are polydiorganosiloxanes containing pendant or telechelic alkenyl groups. As used herein, the term "telechelic" is intended to mean a polymer or copolymer that contains end groups that react selectively to give a bond with another molecule. Suitable alkenyl functional siloxanes and methods for their preparation are described, for example, in U.S. Pat. No. 4,609,574 (Sep. 2, 1986), assigned to the same assignee as the present invention, which is incorporated herein by reference.

In general, these materials can be described as being made up of diorganosiloxane "D" units R$_2$$^a$SiO$_{2/2}$ and chain terminating "M" units R$_3$$^a$SiO$_{1/2}$ R$^a$ where is a methyl radical or a hydrocarbon radical containing unsaturation. The unsaturated radicals (represented above by R1–R18, for example) include higher alkenyl radicals such as —(CH$_2$)$_m$—CH=CH(CH$_2$)$_n$H, where m has a value of 2, 3, or 4; and n has a value of 0, 1, or 2; although m can exceed 4, and n can exceed 2, if desired. The unsaturation need not be in the terminal position of the hydrocarbon. However, it must be at least two carbon atoms removed from the silicon atom.

Polydiorganocyclosiloxanes containing alkenyl groups are also suitable for use according to our invention, and can be represented by the following formulas:

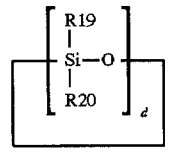

and

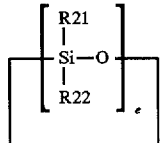

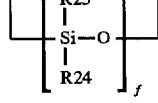

In these formulas, R19–R24 represent an alkyl group containing 1–6 carbon atoms such as methyl, ethyl, propyl, butyl, pentyl, and hexyl, for example; an aryl group such as phenyl; or an alkenyl group. Generally, d, e, and f, have values of 3, 4, 5, and 6, or more. At least one R19–R24 should be an alkenyl group. For example, when R21–R23 are methyl, R24 would an alkenyl radical such as hexenyl.

The conversion of a polydiorganosiloxane containing one alkenyl group to a polydiorganosiloxane containing one aldehyde group by treatment with ozone, followed by treatment with a reducing agent according to our invention, can be represented by reference to the reaction scheme shown below. In this simplified representation, R' is a hydrocarbon linking group, i.e., —(CH$_2$CH$_2$)— preferably containing at least two or more carbon atoms:

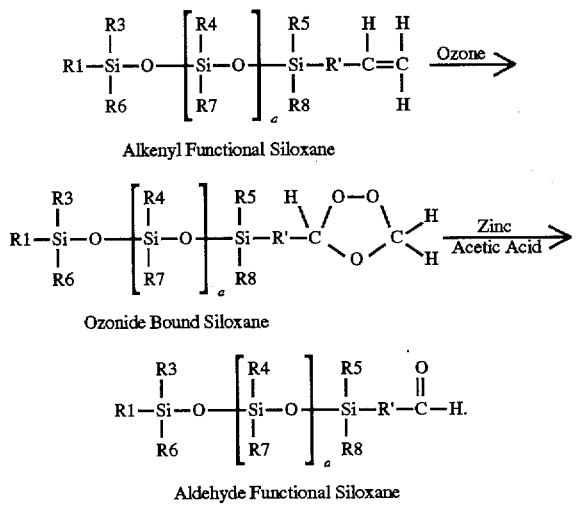

Alkenyl Functional Siloxane

Ozonide Bound Siloxane

Aldehyde Functional Siloxane

According to this scenario, readily available hexenyl functional polysiloxanes, for example, can be converted efficiently and economically to the corresponding Aldehyde Functional Siloxane, by simply subjecting the Alkenyl Functional Siloxane polymer to ozone for a few minutes, and then reducing the ozonide intermediate, i.e., the Ozonide Bound Siloxane, with zinc and acetic acid.

Similarly, conversion of a polydiorganosiloxane containing one alkenyl group to a polydiorganosiloxane containing one ketone group by treatment with ozone, followed by treatment with a reducing agent according to our invention, can be represented by reference to the reaction scheme shown below. In this simplified representation, R' is a hydrocarbon linking group, i.e., —(CH$_2$CH$_2$)—, preferably containing at least two or more carbon atoms, and R" represents an alkyl group such as methyl, or an aryl group such as phenyl, for example:

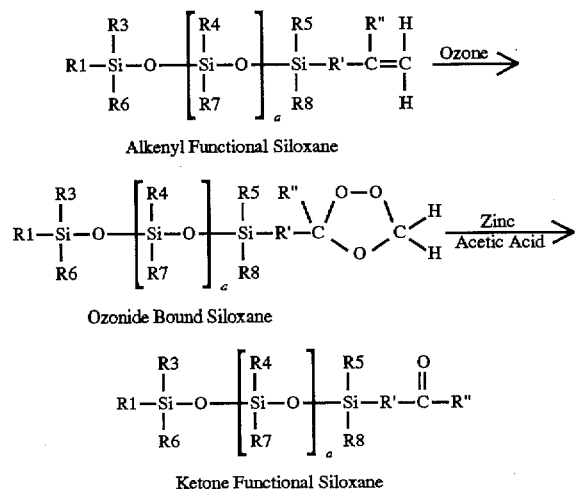

Alkenyl Functional Siloxane

Ozonide Bound Siloxane

Ketone Functional Siloxane

The particular conditions used to carry out these reactions are critical in order to obtain high yields and complete reaction. For example, ozonolysis reactions proceed well at low temperatures usually between −70° to −80° C. However, siloxane polymers and copolymers are either too viscous or crystallize at such low temperatures.

After an extensive search for appropriate conditions, we found that methylene chloride was among one of the most suitable solvents, in addition to chloroform and carbon tetrachloride. However, other suitable solvents that can be employed include pentane, hexane, petroleum ether, cyclohexane, benzene, toluene, methyl chloride, ethyl chloride, ethyl bromide, ethyl acetate, acetone, formamide, ethyl ether, tetrahydrofuran, nitromethane, acetic anhydride, and formic acid. When ozonolysis is carried out at a temperature in the range of about −25° C. to room temperature (20°−25° C.), additional solvents that can be employed include water, acetic acid, trifluoromethane, propyl chloride, and 1,1,2-trichloro-1,2,2-trifluoroethane.

Furthermore, we found that at high concentration of siloxane polymer or copolymer in the solvent during ozonolysis, i.e., above 50 grams in 150 ml, some undesirable crosslinking reactions occurred. Therefore, these undesirable reactions were eliminated by conducting the ozonolysis at lower concentrations of the polymer or copolymer in solution. In addition, the solubility of ozone in the solvent is greater at low temperatures.

The temperature used to carry out the reaction should be higher than the freezing point of the solvent, or higher than the freezing point of the reaction solution. For example, if the solvent used is methylene chloride Which has a freezing point of −97° C., then any temperature higher than −97° C. can be used to carry out the reaction. However, the preferred temperature is any temperature between 15° C. and −30° C.

Depending upon the starting materials selected for use in our process, i.e., the polydiorganosiloxane containing alkenyl groups, a wide range of aldehyde functionalities can be obtained. Representative of some of the most preferred starting materials according to our invention are shown below:

I. Telechelic Polymers corresponding to the formula

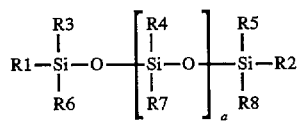

where R1 and R2 are hexenyl; R3 to R8 are methyl, and a is 30, 100, or 200.

II. Pendant and Telechelic Copolymers corresponding to the formula

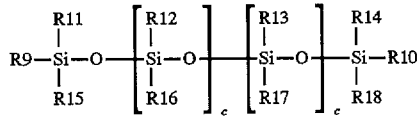

where R9, R10, and R17 are hexenyl; R11 to R16, and R18 are methyl; b is 70, 100, or 150; and the value of c is sufficient to provide 4, 2, and 5 mole percent, respectively, of this methylhexenylsiloxy unit.

III. A Cyclic Siloxane of the formula

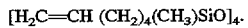

Our invention is illustrated in more detail with reference to the following examples.

EXAMPLE 1

A hexenyl containing polysiloxane corresponding to Pendant and Telechelic Copolymer II shown above where b was 150 and c had a value sufficient to provide 5 mole percent of methylhexenylsiloxy units, was dissolved in methylene chloride (75.71 grams in 150 ml) in a three-neck flask equipped with a stirrer, and the solution was cooled to −78° C. Ozone was introduced into the bottom of the solution and allowed to bubble through the solution at a rate of 0.0213 lb/per hour (0.0268×10$^{-4}$ kilogram per second). However, after about 10 minutes at this temperature, the viscosity of the reaction mixture became too high. It appeared to become frozen such that the ozone could not be introduced effectively throughout the solution. Thus, this reaction was terminated.

EXAMPLE 2

Example 1 was repeated, and the reaction was again conducted at −38° C. However, even at this higher temperature, the solution appeared to freeze, and ozone could not be introduced effectively.

EXAMPLE 3

Example 1 was again repeated, and the same reaction was carried out at 0° C. No freezing or increased viscosity was noted. However, at this higher temperature, methylene chloride was removed from the reaction mixture due to its high volatility, and only the silicone copolymer was left in the reaction flask after one hour. Treatment of the copolymer with Zn and acetic acid was carried out to complete the conversion of any ozonide intermediate that had been formed to an aldehyde. Analysis of the product showed that only trace amounts of aldehyde had been obtained. This example demonstrates that low yields are obtained in the absence of methylene chloride, and indicates that the solvent and the temperature conditions are important variables in the process.

EXAMPLE 4

Example 1 was repeated at −15° C. using a hexenyl containing polysiloxane corresponding to Telechelic Polymer I shown above where a was 100. The ozonolysis reaction was completed in 15 minutes with no apparent loss of solvent or change in the viscosity of the solution. $^{13}$C Nuclear Magnetic Resonance (NMR) indicated complete conversion to the ozonide intermediate by the presence of no residual double bonds. Surprisingly, this ozonide intermediate was stable at room temperature. To convert the ozonide intermediate to the desired aldehyde, it was heated for one hour at 32° C. with Zn and acetic acid.

EXAMPLE 5

Example 4 was repeated using a hexenyl containing polysiloxane corresponding to Telechelic Polymer I shown above where b was 30. The ozonolysis reaction was completed in 30 minutes with no apparent loss of solvent or change in viscosity. $^{13}$C NMR clearly showed the disappearance of the original double bond in the hexenyl group, and the formation of the desired aldehyde terminated polysiloxane. A longer reaction time was used in this example compared to the reaction time used in Example 4 (i.e., 30 minutes compared to 15 minutes, respectively), due to a higher concentration of double bond in the solution.

EXAMPLE 6

Example 4 was repeated using a hexenyl containing polysiloxane corresponding to Pendant and Telechelic Copolymer II shown above where b was 150 and c had a value sufficient to provide 5 mole percent of methylhexenylsiloxy units. The ozonolysis was terminated after 5 minutes due to excessive foaming and increased viscosity.

EXAMPLE 7

Example 4 was repeated using a hexenyl containing polysiloxane corresponding to Pendant and Telechelic Copolymer II shown above where b was 70 and c had a value sufficient to provide 4 mole percent of methylhexenylsiloxy units. However, in this example, a lower concentration of Copolymer in methylene chloride was used, i.e., 30 grams in 150 ml. The ozonolysis reaction was completed in 15 minutes with no apparent loss of solvent or change in viscosity. $^{13}$C NMR indicated complete conversion of the double bond to the desired aldehyde, and confirmed the presence of both terminal and pendant aldehyde groups, with no trace of double bonds after treatment with Zn and acetic acid.

EXAMPLE 8

Example 6 was repeated using a hexenyl containing polysiloxane corresponding to Pendant and Telechelic Copolymer II shown above where b was 150 and c had a value sufficient to provide 5 mole percent of methylhexenylsiloxy units. Again, a lower concentration of Copolymer in methylene chloride was employed (30 grams in 150 ml). The ozonolysis reaction was completed in 15 minutes with no apparent loss of solvent or change in viscosity. $^{13}$C NMR indicated complete conversion of the double bond to the desired aldehyde, and confirmed the presence of both terminal and pendant aldehyde groups, with no trace of double bonds after treatment with Zn and acetic acid.

EXAMPLE 9

A hexenyl containing cyclic polysiloxane (43 grams) of the formula

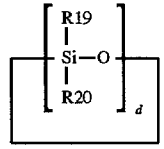

where R19 was methyl, R20 was hexenyl H$_2$C=CH(CH$_2$)$_4$−, and d was 4, was dissolved in 150 mL of methylene chloride in a three liter flask equipped with a stirrer, and the solution was cooled to −15° C. Ozone was introduced into the bottom of the solution and allowed to bubble through the solution at a rate of 0.0213 lb/per hour (0.0268×10$^{-4}$ kilogram per second). The ozonolysis reaction was completed in about 40 minutes. No freezing, increased viscosity, or solvent loss was observed. To convert the ozonide intermediate to the corresponding aldehyde, it was heated for one hour at room temperature (25° C.) with Zn and acetic acid. $^{13}$C Nuclear Magnetic Resonance (NMR) indicated complete conversion from the ozonide intermediate to the desired aldehyde by the presence of no residual double bonds.

EXAMPLE 10—COMPARISON

For comparison, an ozonolysis reaction was conducted using 1-hexene CH$_3$CH$_2$CH$_2$CH$_2$CH=CH$_2$ (8.5 grams) in methylene chloride (150 ml) at −78° C. for 30 minutes. A very unstable ozonide was obtained. It rapidly decomposed in an uncontrolled exothermic reaction, and splashed out of the reaction flask shortly after it had been treated with zinc and acetic acid.

Example 10 demonstrates that the presence of the siloxane, as in Examples 4–9, greatly moderates the rate of the decomposition reaction, and reduces the explosion risk, although extreme care is still recommended when dealing with highly oxygenated and unstable ozonide intermediates.

The advantage of our process is its simplicity, and its capability of using readily available starting materials. Further, the reaction is relatively fast, and leads to high yields with little or no complications associated with by-products. The aldehyde functional polysiloxanes, in particular, can be used as crosslinking agents, i.e., as in the reaction of an aldehyde with an amine. Thus, when an aldehyde functional polysiloxane is added to amine functional polysiloxane, a very effective crosslinking reaction will take place. Similarly, addition of an aldehyde functional polysiloxane to an alcohol will also lead to a crosslinked system.

Other variations may be made in compounds, compositions, and methods described herein without departing from the essential features of our invention. The forms of our invention are exemplary only and not intended as limitations on its scope as defined in the appended claims.

We claim:

1. A method of making an organosiloxane containing carbonyl functionality, the method comprising (I) forming an organosiloxane containing ozonide functionality by exposing to ozone an organosiloxane having a formula selected from the group consisting of

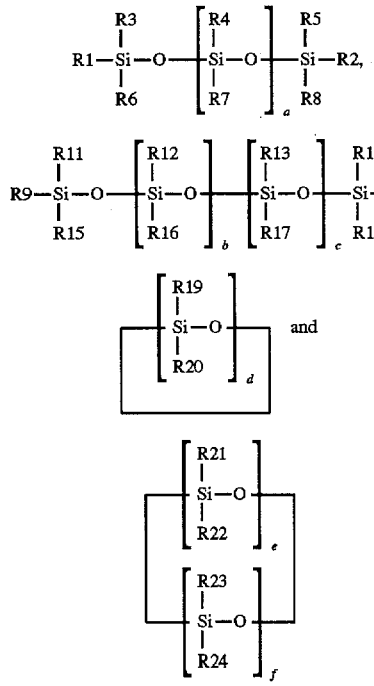

where R1–R24 in each formula represent an alkyl group containing 1–6 carbon atoms; an aryl group; or an alkenyl group; with the proviso that at least one R1–R24 group in each formula is an alkenyl group with the unsaturated carbon atoms separated from the silicon atom by at least two saturated carbon atoms; a and b have a value of 1–200; c has a value of about 1–10; and d-f have a value of 3–6;

and (II) reducing the resulting organosiloxane containing ozonide functionality to an organosiloxane containing carbonyl functionality.

2. A method according to claim 1 in which (i) R1 and R2 are both alkenyl groups; (ii) R1, R2, and either R4 or R7 are alkenyl groups simultaneously; (iii) R9 and R10 are both alkenyl groups; (iv) R9, R10, and either R13 or R17 are alkenyl groups simultaneously; or (v) R12 and R16 are both alkyl groups and at least one group R9–R11, R13–R15, R17, or R18 is an alkenyl group; and any alkenyl group in (i)-(v) is represented by the formula —(CH$_2$)$_m$—CH=CH(CH$_2$)$_n$H where m has a value of 2, 3, 4, or more, and n has a value of 0, 1, 2, or more.

3. A method according to claim 1 in which the organosiloxane containing ozonide functionality is reduced to the organosiloxane containing carbonyl functionality with a reducing agent selected from the group consisting of sodium iodide, potassium iodide, zinc, magnesium, sodium bisulfite, ferrous sulfate, potassium ferrocyanide, stannous chloride, tin, ferrous ammonium sulfate, silver nitrate, trimethyl phosphite, quinol, pyridine, piperidine, sulfur dioxide, and dimethyl sulfide.

4. A method according to claim 3 in which the organosiloxane containing ozonide functionality is reduced to the organosiloxane containing carbonyl functionality with a reducing agent in the presence of a solvent selected from the group consisting of methylene chloride, chloroform, carbon tetrachloride, pentane, hexane, petroleum ether, cyclohexane, benzene, toluene, methyl chloride, ethyl chloride, ethyl bromide, ethyl acetate, acetone, formamide, ethyl ether, tetrahydrofuran, nitromethane, acetic anhydride, formic acid, water, acetic acid, trifluoromethane, propyl chloride, and 1,1,2-trichloro-1,2,2-trifluoroethane.

5. A method according to claim 4 in which step (I) of the method is carried out at a temperature above the freezing point of the solvent.

6. An organosiloxane containing carbonyl functionality comprising an organosiloxane selected from the group consisting of

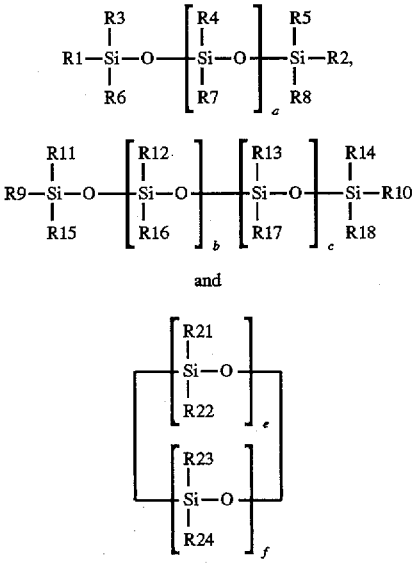

where R1–R18 and R21–R24 are alkyl groups with 1–6 carbon atoms; an aryl group; a substituent containing an aldehyde radical

separated by at least two carbon atoms from the silicon atom; or a substituent containing a ketone radical

in which R25 represents an alkyl group or an aryl group; with the proviso that at least one R1–R18 and R21–R24 group in each formula is the substituent containing an aldehyde radical or the substituent containing a ketone radical; a has a value of 4–200; b has a value of 1–200; c has a value of about 1–10; and e and f have a value of 3–6.

7. An organosiloxane containing aldehyde functionality comprising an organosiloxane selected from the group consisting of

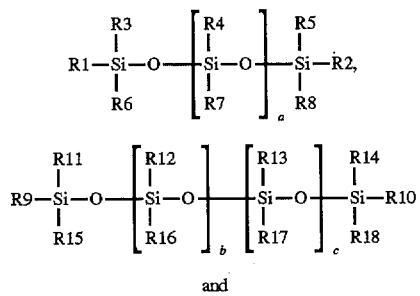

and

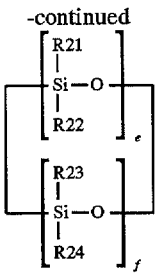

where R1–R18 and R21–R24 are alkyl groups with 1–6 carbon atoms; an aryl group; a substituent containing an aldehyde radical

separated by at least two carbon atoms from the silicon atom; with the proviso that at least one R1–R18 and R21–R24 group in each formula is the substituent containing an aldehyde radical; a has a value of 4–200; b has a value of 1–200; c has a value of about 1–10; and e and f have a value of 3–6.

* * * * *